(12) United States Patent
Cross, Jr. et al.

(10) Patent No.: US 11,912,642 B2
(45) Date of Patent: Feb. 27, 2024

(54) PROCESSES FOR PREPARING HYDROCARBON COMPOSITIONS

(71) Applicant: KOCH TECHNOLOGY SOLUTIONS, LLC, Wichita, KS (US)

(72) Inventors: William M. Cross, Jr., Wilmington, DE (US); Daniel Travis Shay, Media, PA (US); Rui Chi Zhang, Beijing (CN); Feng Hao Zhang, Beijing (CN); Fang Zhang, Beijing (CN)

(73) Assignee: KOCH TECHNOLOGY SOLUTIONS, LLC, Wichita, KS (US)

( * ) Notice: Subject to any disclaimer, the term of this patent is extended or adjusted under 35 U.S.C. 154(b) by 317 days.

(21) Appl. No.: 16/772,806

(22) PCT Filed: Dec. 14, 2018

(86) PCT No.: PCT/US2018/065641
§ 371 (c)(1),
(2) Date: Jun. 15, 2020

(87) PCT Pub. No.: WO2019/118825
PCT Pub. Date: Jun. 20, 2019

(65) Prior Publication Data
US 2021/0206703 A1    Jul. 8, 2021

Related U.S. Application Data

(60) Provisional application No. 62/608,111, filed on Dec. 20, 2017, provisional application No. 62/599,275, filed on Dec. 15, 2017.

(51) Int. Cl.
*C07C 2/12* (2006.01)
*B01J 29/40* (2006.01)
(Continued)

(52) U.S. Cl.
CPC .................. *C07C 2/12* (2013.01); *B01J 29/40* (2013.01); *B01J 35/023* (2013.01); *B01J 38/04* (2013.01); *C07C 7/12* (2013.01); *C07C 2529/40* (2013.01)

(58) Field of Classification Search
CPC ......... C07C 2/12; C07C 7/12; C07C 2529/40; C07C 2/04; C07C 2/08; C07C 5/22;
(Continued)

(56) References Cited

U.S. PATENT DOCUMENTS 3,767,568 A  *  10/1973  Chen ........................ B01J 29/70
                                                                208/65
3,960,978 A       6/1976  Givens et al.
(Continued)

FOREIGN PATENT DOCUMENTS

EP        0250879 A1     1/1988
WO     2008147546 A1    12/2008
WO     2010104762 A1     9/2010

OTHER PUBLICATIONS

International Search Report and Written Opinion for International Application No. PCT/US18/65641, dated Mar. 4, 2019, 11 pages.
(Continued)

*Primary Examiner* — Thuan D Dang

(57) ABSTRACT

Processes, catalysts and systems for preparing a composition comprising aliphatic, olefinic, cyclic and/or aromatic hydrocarbons of seven or greater carbon atoms per molecule are provided.

21 Claims, 1 Drawing Sheet

(51) Int. Cl.
*B01J 35/02* (2006.01)
*B01J 38/04* (2006.01)
*C07C 7/12* (2006.01)

(58) Field of Classification Search
CPC . B01J 29/40; B01J 35/023; B01J 38/04; B01J 29/42; B01J 29/44; B01J 29/48; Y02P 20/584; C10G 11/05; C10G 35/085; C10G 35/095
See application file for complete search history.

(56) References Cited

U.S. PATENT DOCUMENTS

| | | | |
|---|---|---|---|
| 3,992,468 A | 11/1976 | Cosyns et al. | |
| 4,753,720 A * | 6/1988 | Morrison | C10G 35/095 585/419 |
| 4,855,524 A | 8/1989 | Harandi et al. | |
| 4,950,823 A * | 8/1990 | Harandi | C07C 2/66 585/446 |
| 5,043,517 A * | 8/1991 | Haddad | B01J 29/90 585/533 |
| 5,395,513 A * | 3/1995 | Chin | C10G 35/09 208/135 |
| 5,603,824 A | 2/1997 | Kyan et al. | |
| 5,792,338 A | 8/1998 | Gosling et al. | |
| 2006/0163116 A1 | 7/2006 | Baptista et al. | |
| 2007/0100182 A1 | 5/2007 | Coupard et al. | |
| 2008/0021251 A1 | 1/2008 | Iaccino et al. | |
| 2010/0247391 A1 | 9/2010 | Nicholas et al. | |
| 2010/0249474 A1 | 9/2010 | Nicholas et al. | |
| 2010/0249479 A1 | 9/2010 | Berg-Slot et al. | |
| 2010/0249480 A1 | 9/2010 | Nicholas et al. | |
| 2011/0132804 A1 | 6/2011 | Stevenson et al. | |
| 2014/0024870 A1 | 1/2014 | Nicholas et al. | |
| 2014/0336432 A1 | 11/2014 | Bao et al. | |
| 2017/0129828 A1 | 11/2017 | Davies et al. | |

OTHER PUBLICATIONS

International Preliminary Report on Patentability for International Application No. PCT/US18/65641, dated Jun. 16, 2020, 9 pages.

\* cited by examiner

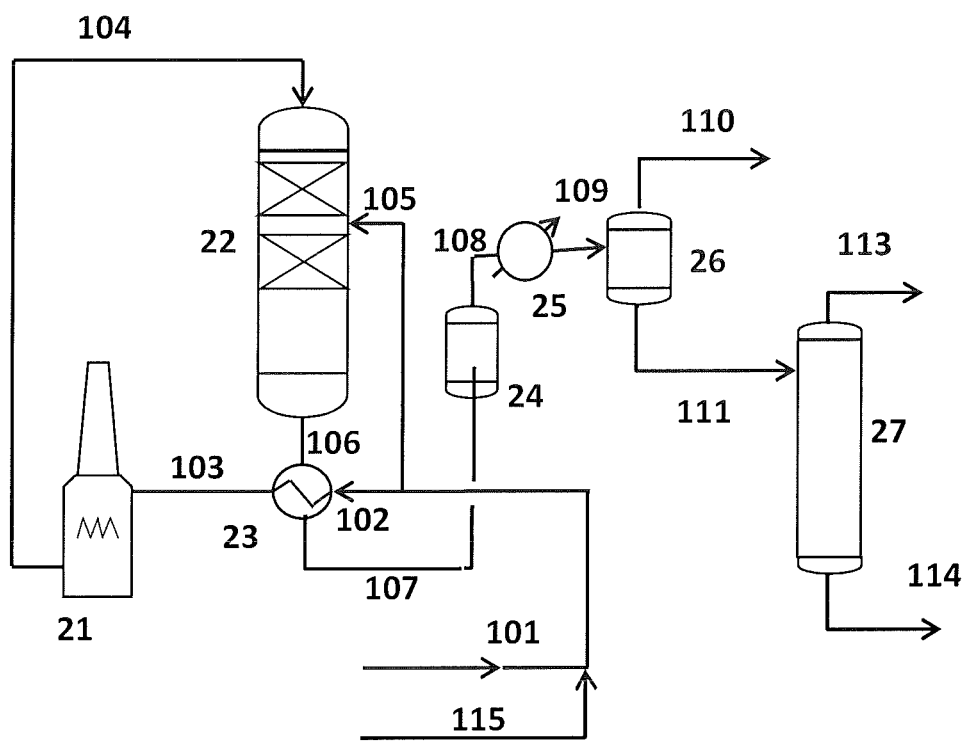

PROCESSES FOR PREPARING HYDROCARBON COMPOSITIONS

This patent application is a National Phase of International Application No. PCT/US18/65641, filed on Dec. 14, 2018 which claims the benefit of priority from U.S. Provisional Application Ser. No. 62/608,111, filed Dec. 20, 2017 and U.S. Provisional Application Ser. No. 62/599,275, each of which is incorporated herein by reference in their entireties

BACKGROUND

Exploitation of shale gas and shale-oil resources in the United States, and elsewhere, involves production of substantial quantities of natural gas liquids (NGLs), sometimes referred to as condensate. Such condensate can comprise ethane, propane, butane, pentane and hexane, for example. While the methane content of shale gas can be used as a source of natural gas, maximizing the value of the "heavier" components is key to maintaining the profitability of shale gas production.

Condensate, in this context, is typically separated from natural gas, ethane and liquefied petroleum gas (or LPG) in gas separation plants. The condensate comprises straight-chain pentane and hexane and is both low octane and has a high vapor pressure. As such, it is generally unsuitable for use in the gasoline fuel pool. Instead, the condensate is used as a feedstock for olefin steam crackers as an alternative to ethane or refinery naphtha, accordingly commanding a significantly lower value than gasoline.

As refineries switch from heavier sources of crude oil to lighter crudes, which originate in shale deposits, the proportion of light paraffinic naphtha generally increases. As a result, the straight run naphtha produced from the crude fractionator contains large quantities of straight chain pentane and hexane, which has a relatively low octane number or unit and relatively high vapor pressure. Further processing of this stream to reduce sulfur content by hydrotreating further reduces the octane content as a result of hydrogenation of unsaturated species such as olefins.

One means by which it is possible to increase octane content is isomerization, to increase the proportion of branched paraffins. However, this has the effect of further increasing the vapor pressure of the stream and therefore, is not a feasible route for use of the stream in gasoline blend stocks.

U.S. Pat. No. 3,960,978 discloses metalized (cation exchanged) zeolytes, such as ZSM-5 & ZSM-11, that comprise metals such as Zn, Cr, Pt, Pd, Ni, and Re, for example, in a process technology referred to as M-Forming™ (Chen et al., 1986). The general understanding is that the ion exchange adds oligomerization capability to the aromatization functionality within the zeolite matrix that is said to and may enable the conversion of low molecular weight olefins, such as propylene, into oligomers and aromatics, via the catalyst's dehydrocyclization functionality. The U.S. refining industry has not however, widely utilized this technology, presumably because it is not economically favorable and/or technically impractical, unduly complex.

Catalyst applications substantially involving crystalline zeolites are also known. For example, Published U.S. Patent Application Nos. 2010/0247391, 2010/0249474, 2010/0249480, and 2014/0024870, describe processes using amorphous silica alumina materials containing Group VIII & Group VIB metals for C5+ oligomer production.

Against this background it is apparent that improved materials and methods are needed to produce more valuable hydrocarbon mixtures from such streams.

SUMMARY

The present invention relates to materials and processes for preparing a composition comprising, for example, aliphatic, olefinic, cyclic and/or aromatic hydrocarbons of five or greater carbon atoms per molecule.

In one nonlimiting embodiment, the process comprises providing a first hydrocarbon mixture comprising isomers of hydrocarbons. The process further comprises providing a heterogeneous catalyst comprising pentasil zeolite; amorphous silica, amorphous alumina, or a combination thereof; Zn and/or Cu; and at least one exchanged metal of Group VII (comprising manganese, technetium, rhenium and bohrium) series in a range of about 0.05% to about 6% by weight.

The first hydrocarbon mixture is then contacted with the heterogeneous catalyst to form a second hydrocarbon mixture comprising molecules having five or more carbon atoms.

In some nonlimiting embodiments of any of the processes described herein, the process may further comprise stopping formation of the second hydrocarbon mixture, isolating the heterogeneous catalyst, and regenerating the heterogeneous catalyst to remove carbonaceous deposits.

In some nonlimiting embodiments of any of the processes described herein, the processes may further comprising heating or transferring heat to the first hydrocarbon mixture using one or more cross-exchangers.

In some nonlimiting embodiments of any of the processes described herein, the processes may further comprise use of a sulfur removal member.

In some nonlimiting embodiments of any of the processes described herein, the first hydrocarbon mixture is obtained from straight run naphtha derived from a crude oil distillation unit or from a natural gasoline or condensate.

In some nonlimiting embodiments of any of the processes described herein, the processes further comprise providing a liquid petroleum gas (LPG) composition comprising C3 or C4 hydrocarbons, or combinations thereof with the first hydrocarbon mixture comprising isomers of C5 or C6 hydrocarbons or combinations thereof.

In one nonlimiting embodiment of any of the processes described herein, the present invention relates to a process for preparing a composition comprising straight-chain, olefinic, cyclic and/or aromatic hydrocarbons of five or greater carbon atoms per molecule according to FIG. 1.

Processes of the present invention are useful in upgrading light naphtha into higher molecular weight paraffins, naphthenics, and aromatics. Resulting upgraded naphtha products produced by these processes are of high octane and may be directly useful as a gasoline blendstock or as feed to an extraction process for aromatics production.

BRIEF DESCRIPTION OF THE FIGURES

FIG. 1 is a process diagram depicting a nonlimiting embodiment of conversion of naphtha using a Multibed downflow reactor in accordance with the present invention.

DETAILED DESCRIPTION

This disclosure relates to processes for preparing a composition comprising aliphatic, olefinic, cyclic and/or aromatic hydrocarbons of five or greater carbon atoms per molecule. In one nonlimiting embodiment, the processes are for preparing a composition comprising aliphatic, olefinic, cyclic and/or aromatic hydrocarbons of six or greater carbon atoms per molecule. In one nonlimiting embodiment, the processes are for preparing a composition comprising aliphatic, olefinic, cyclic and/or aromatic hydrocarbons of seven or greater carbon atoms per molecule. The processes of the present invention employ a robust catalyst which can handle small quantities of sulfur, an economical choice of a fixed bed reactor design which preferably includes at least two beds of catalyst, and in some embodiments, integrated sulfur removal by adsorbent to meet latest tier 3 sulfur specifications in gasoline.

The processes of the present invention comprise providing a first hydrocarbon mixture comprising isomers of hydrocarbons. In one nonlimiting embodiment, the first hydrocarbon mixture comprises isomers of hydrocarbons containing five to seven carbon atoms. In some nonlimiting embodiments, the first hydrocarbon mixture is obtained from straight run naphtha derived from a crude oil distillation unit or from a natural gasoline or condensate.

Processes of the present invention further comprise providing a heterogeneous catalyst.

The heterogeneous catalyst comprises pentasil zeolite. In one nonlimiting embodiment, the pentasil zeolite comprises crystalline aluminosilicate silica/alumina at a mole ratio of between about 15 and about 100. In one nonlimiting embodiment, the pentasil zeolite comprises ZSM5.

In one nonlimiting embodiment, the pentasil zeolite is included in the catalyst in a range between about 1% to about 99% by weight of the total catalyst. In one nonlimiting embodiment, the pentasil zeolite is included in the catalyst in a range of between about 20% to about 85% by weight of the total catalyst. The heterogeneous catalyst further comprises amorphous silica, amorphous alumina, or a combination thereof. In one nonlimiting embodiment, the zeolite comprises a mixture, of silica and alumina.

In one nonlimiting embodiment, the silica, alumina, or a combination thereof is included in the catalyst in a range between about 1% to about 99% by weight of the total catalyst.

In addition, the heterogeneous catalyst comprises Zn, CU or both. In one nonlimiting embodiment, the Zn, Cu or both are included in a range between about 0.05% to about 3% by weight of the total catalyst.

Further, the heterogeneous catalyst comprises at least one exchanged metal of the Group VII series. In one nonlimiting embodiment, at least one of the Group VII series metals exchanged to produce the heterogeneous catalyst is Rhenium.

In one nonlimiting embodiment, the metal is in the range of about 0.05% to about 6% by weight of the total catalyst.

In one nonlimiting embodiment, the metal is in the range of about 0.5% to about 6% by weight.

In one nonlimiting embodiment, the heterogeneous catalyst is sized to achieve a weight hourly space velocity in the range about 0.01/hour to about 100/hour, where weight hourly space velocity is defined as mass flow of feed in kg/h divided by the mass of catalyst in kg.

In one nonlimiting embodiment, the first hydrocarbon mixture is contacted with the heterogeneous catalyst at a temperature of between about 200° C. and 500° C., and at a pressure of between 1 barA and 20 barA. Typically the first hydrocarbon mixture is present as a gaseous stream when it is contacted with the catalyst.

In one nonlimiting embodiment, the catalyst used within the process comprises the zeolite ZSM-5 at concentrations between 20-85% weight, Zn, Cu or both Zn and Cu at a concentration less than 3% weight and one element of Group VII at concentration less than 5% weight, along with an amorphous binder comprising silica and/or alumina. This exemplary catalyst provides high conversion of pentane or hexane at conditions between 200-400° C. and at operational pressures below 30 barg.

In one nonlimiting embodiment, the processes further comprise providing a dilution stream of liquid petroleum gas (LPG) composition comprising three and/or four carbon atoms per molecule with the first hydrocarbon mixture.

The processes further comprise contacting the first hydrocarbon mixture with the heterogeneous catalyst to form a second hydrocarbon mixture. In one nonlimiting embodiment, the second hydrocarbon mixture has a higher linear octane number. In one nonlimiting embodiment, the second hydrocarbon mixture comprises hydrocarbons having five or more carbon atoms. In one nonlimiting embodiment, the second hydrocarbon mixture comprises hydrocarbons having six or more carbon atoms. In one nonlimiting embodiment, the second hydrocarbon mixture comprises hydrocarbons having seven or more carbon atoms.

As will be understood by the skilled artisan upon reading this disclosure, in addition to higher linear octane number, motor octane units and/or research octane units can be routinely obtained.

In one nonlimiting embodiment, the second hydrocarbon mixture has a higher linear octane number or unit and a lower vapor pressure as compared to the first hydrocarbon mixture. In one nonlimiting embodiment, the second hydrocarbon mixture has a higher octane unit of about 10 units. In one nonlimiting embodiment, the second hydrocarbon mixture has a higher octane unit of about 15 units. In one nonlimiting embodiment, the second hydrocarbon mixture has a higher octane unit of about 20 units. In one nonlimiting embodiment, the second hydrocarbon mixture has a higher octane unit of about 25 units.

In one nonlimiting embodiment, the heterogeneous catalyst is within one or more bed members. Preferred, as an economical choice, is use of a fixed bed reactor design which includes at least two beds of catalyst.

In one nonlimiting embodiment, each bed member comprises one or more first hydrocarbon mixture feed points.

In one nonlimiting embodiment, the first hydrocarbon mixture is contacted with the heterogeneous catalyst using a temperature control member to control the temperature of the first hydrocarbon mixture. In one nonlimiting embodiment, the temperature control member is located on or about the one or more first hydrocarbon mixture feed points.

In some nonlimiting embodiments, the processes further comprise stopping formation of the second hydrocarbon mixture by isolating the feed on first hydrocarbon mixture from the heterogeneous catalyst. This is typically accomplished by means of one or more isolation valves in the feed-line to the catalyst. Hydrocarbons that are present in the catalyst are removed using nitrogen and or steam prior to commencing the regenerating process. The heterogeneous catalyst is regenerated to remove carbonaceous deposits. In one nonlimiting embodiment, the temperature of the catalyst during regeneration is about 200° C. to 700° C. In one nonlimiting embodiment, the regenerating comprises passing heated wet or dry nitrogen, air or combinations thereof over the heterogeneous catalyst. Typically the catalyst is regenerated by passing a stream of heated gas through the catalyst for a period of between 1 hour and 10 days. Initially the gas stream is heated nitrogen. Air is added to the nitrogen to provide an oxidant. The oxidant oxidizes carbonaceous materials which accumulate on the surface of the catalyst and affect its catalytic activity. The typical flowrate of nitrogen is 0.5-2 kg/h for every kg of catalyst. The flowrate of air is adjusted to maintain an oxygen content in the feedstream of between 1 and 20% v/v. Steam may be added to the regenerating gas stream to improve the regenerating process. The temperature of the regenerating gas stream that is supplied to the catalyst is progressively increased during regeneration process within the range 200-700° C.

In one nonlimiting embodiment, the heterogeneous catalyst is within one or more bed members. Preferred, as an economical choice, is use of a fixed bed reactor design which includes at least two beds of catalyst. In this nonlimiting embodiment, the heated wet or dry nitrogen, air or combinations thereof is supplied to each bed catalyst bed member in parallel via the one or more first hydrocarbon mixture feed points. This nonlimiting embodiment with at least two beds of catalyst can be particularly useful, whereby one is operating, while the other reactor is regenerated. These reactors are designed, such that either one may be taken off-line from the processing of the naphtha and regenerated periodically using air and nitrogen.

In some nonlimiting embodiments, the processes further comprise transferring heat using one or more cross-exchangers or heating the first hydrocarbon mixture to a temperature of between 250 and 500° C. using one or more cross-exchangers.

In some nonlimiting embodiments, the processes further comprise obtaining a liquid, semi-liquid, gaseous or semi-gaseous mixture, isolated downstream of the at least one cross-exchanger. The hydrocarbon liquid, typically comprising straight-chain, olefinic, cyclic and/or aromatic hydrocarbons of five, six, seven or greater carbon atoms per molecule, is typically obtained by either condensing the volatile components that are present in the second hydrocarbon mixture, where such condensation occurs when the stream is cooled in a heat exchange or combination of heat exchangers. The liquids may also be obtained by contacting the second hydrocarbon mixture with and absorbent liquid such as a heavier hydrocarbon stream, or a organic solvent stream. Contacting the second hydrocarbon stream with a absorbent liquid may be also be used in conjunction with a series of heat exchange units.

In some nonlimiting embodiments, the processes further comprise using a sulfur removal member, which is typically located downstream of the heterogeneous catalyst, such that it removes sulfur from the second hydrocarbon mixture. In one nonlimiting embodiment, the sulfur removal member comprises an adsorbent. In one nonlimiting embodiment, the adsorbent comprises metal oxide. In one nonlimiting embodiment, the sulfur removal member is operated at a temperature capable of removing sulfur. In one nonlimiting embodiment, the sulfur removal member is operated at a temperature of between about 80° C. to 200° C.

In some nonlimiting embodiments, the second hydrocarbon mixture is isolated in a drum, absorption tower, or distillation column, or combinations thereof.

In one nonlimiting embodiment, the present invention provides a process solution to upgrade light naphtha feedstocks, such as straight run naphtha, or condensate, and convert them into higher boiling range naphtha with increased octane number or unit and lower vapor pressure, which can be useful as gasoline blend stock.

A process diagram for the conversion of light naphtha, to form a heavier higher boiling-range material, containing aromatics, is provided in FIG. 1. The purpose of the process is to substantially convert light paraffinic compounds such as hexane and pentane, which have a high proportion of straight chain isomers, into larger paraffinic naphthenic, and aromatic components, such that they can used as high octane gasoline.

As shown in FIG. 1, the light naphtha feed comprising, for example, pentane and hexane enters the process as a liquid in stream 101. The remaining stream 102 is further split into two streams 102 and 105. Stream 102 is sent through exchangers and heaters prior to reaction. Cross-exchanger 23, uses the hot reactor effluent to heat the cold inlet feed stream, stream 102. Typical temperatures of approximately 150 to 300° C. are achieved using the cross-exchanger, resulting in stream 103. Stream 103 is further heated to a reaction temperature of approximately 200 to 500° C. using fired heater 21. Hot gas feed 104 enters the top of reactor 22 and flows downward where it is at least partially reacted over a $1^{st}$ catalyst bed containing a zeolite catalyst. Cooler feed 105 may be injected into the reactor to reduce the temperature prior to being introduced into the second catalyst bed. The combined effluent from the $1^{st}$ catalyst bed and cooler feed injection 105, if used, are then further reacted over a $2^{nd}$ catalyst bed. Hot reactor effluent 106 exits the reactor and is cooled using cross-exchanger 23. The cooled stream 107 is processed in an optional sulfur removal bed 24, which adsorbs sulfur components. The desulfurized stream 108 is cooled in cooler 25. The resulting product stream 109, containing 2-phase liquid and vapor products are separated in vessel 26. The majority of methane and ethane, which are produced as by-products in reactor 22, exit the process in stream 110. The remaining stream is further processed in fractionation column 27 where LPG components such as propane and butane are removed as the top product 113, while the upgraded naphtha in stream 114 is directed to the gasoline pool.

In one nonlimiting embodiment, the present invention relates to a process according to FIG. 1 for preparing a composition comprising straight-chain, olefinic, cyclic and/or aromatic hydrocarbons of five, six, seven or greater carbon atoms per molecule.

An alternative nonlimiting embodiment of the naphtha upgrading process involves co-injection of LPG comprising mainly butane or propane in stream 115. An advantage of this process is that any olefin compounds present in the LPG are converted into gasoline compounds. In addition, the light olefinic material helps to initiate the upgrading reactions, increasing the octane content of the resulting naphtha.

The process flow diagram provided herein is a nonlimiting illustration of the general process. Upon reading this disclosure, the skilled artisan would understand that certain derivations known to those skilled in the art, such as, but in no way limited to, further integration with conventional FCC light-ends recovery equipment, various heat integration options and product stabilization process can be used.

The following nonlimiting examples are provided to further illustrate the present invention. A nonlimiting example of a catalyst useful in conjunction with the illustrated process and comprising pentasil zeolite in a range between about 1% to about 99%; amorphous silica, amorphous alumina, or a combination thereof, in a range of about 1% to about 99%; Zn and/or Cu, in a range between about 0.05% to about 3% by weight; and at least one exchanged metal of Group VII series in a range of about 0.05% to about 6% by weight is set forth in Example 1. Process performance of this catalyst, is disclosed by Examples 2, 3, 4 and 5.

EXAMPLES

Example 1: Catalyst 75 grams ZSM5 powder with a Si/Al ratio of 15/1 was mixed with 20 grams of kaolin, 5 grams of carboxymethyl cellulose and enough water to form a suitable paste for extrusion after mixing in a high shear sigma blade mixer. After extrusion through a short L/D ratio multiple 3 mm trilobe geometry die plate extruder, the green extrudate was dried at 120° C. in air for 3 hours followed by calcination in air at 650-750° C. for 3 hours. After calcination, sodium exchange was performed with aqueous salts of zinc, rhenium and copper to achieve a metal loading of 1 weight percent for each metal respectively. After ion exchange, the extrudate was dried in air at 120° C. for 3 hours followed by calcination to 650-750° C. for 3 hours. After final calcination, the catalyst was prepared for activity test in a fixed bed reactor.

Example 2: 12 Hour Average Catalyst Performance, from a Time on Stream of 96-140 Hours 10 grams of 16 mesh particle size catalyst was loaded into a 0.500 inch diameter 316 SS reactor tube, equipped with a thermocouple, located in the middle of the catalyst bed, with glass beads above and below. The reactor tube was then placed in an electric tube furnace. The reactor tube was heated to 300° C. under a constant flow of research grade nitrogen, while maintaining a back pressure of 9 barg.

Once the internal catalyst bed temperature stabilized at 300° C., the nitrogen feed was discontinued and 0.4 weight hour space velocity of n-hexane was introduced to the reactor, while maintaining a backpressure of 9 barg. The catalyst bed temperature of 300° C. was maintained for 24 hours under the constant hydrocarbon feed; after which, it was increased to 350° C. at a rate of 1° C./minute. The gaseous product stream was analyzed on-line by an Agilent 7890B gas chromatograph, while the liquid product stream was analyzed periodically offline by an Agilent 7890B gas chromatograph to confirm C4+ yield and feed conversion in the condensate. Detailed hydrocarbon analysis was obtained by employing the ASTM D6730 method. The 12 hour average catalyst performance, from a time on stream of 96-140 hours, is provided in the table below.

| Catalyst Bed Temperature | WHSV | Hexane Conversion | Hexane Yield to Methane/ethane | Hexane Yield to $C_3$ hydrocarbon | Hexane Yield to $C_4$ hydrocarbon | Hexane Yield to $C_5+$ hydrocarbon |
| --- | --- | --- | --- | --- | --- | --- |
| 350° C. | 0.4 | 98.2% | 1.5% | 15.8% | 9.7% | 69.0 |

The $C_5+$ Product Composition was measured on a mass percentage. This GC analysis was as follows:

| Benzene | Toluene | C8 aromatic |
| --- | --- | --- |
| 2.6% | 11.9% | 15.5 |

Example 3: 10 Hour Average Catalyst Performance from a Time on Stream of 100-110 Hours The procedure of Example 2 was repeated for the catalyst of Example 1. The reactor was heated to 300° C., and the nitrogen feed was discontinued and 0.4 WHSV of an n-pentane was introduced at a back pressure of 9 barg. The reactor was slowly heated to 353° C. and the conditions were held constant for 100 hours. The table below is the 10 hour average catalyst performance from a time on stream of 100-110 hours.

| Catalyst Bed Temperature | WHSV | n-pentane conversion | Pentane Yield to methane/ethane | Pentane Yield to $C_3$ hydrocarbon | Pentane Yield to $C_4$ hydrocarbon | Pentane Yield to $C_5+$ hydrocarbon |
| --- | --- | --- | --- | --- | --- | --- |
| 353° C. | 0.4 | 96.5% | 1.1% | 12.5% | 11.8 | 74.6 |

The C$_5$+ Product Composition on a mass percentage basis is as follows:

| benzene | toluene | C8 aromatic |
|---|---|---|
| 3.6% | 9.2% | 20.2% |

Example 4: Mixed Naphtha Feed Together with LPG Diluent

A reactor operated with a mixed naphtha feed together with LPG diluent. The reactor was operated at a temperature in the range 280-420° C., preferably 350° C. and a pressure of 9 barg. The feed rate was equivalent to a space velocity. Average reactor performance at the above conditions was as follows:

| Catalyst Bed Temperature | WHSV | naphtha conversion | Yield to methane/ ethane | Yield to C$_3$/C$_4$ hydrocarbon | Yield to C$_5$+ hydrocarbon | Octane increase |
|---|---|---|---|---|---|---|
| 353° C. | 0.4 | 96.5% | 1.1% | 15-20% | 75-80% | 20-25 points |

Example 5: Mixed Naphtha Feed Together with LPG Diluents and a Sulfur Removal Bed A reactor is operated with a mixed naphtha feed of 10,000-12,000 kg/h containing 90 ppm sulfur, together with LPG diluent flow of 2000 kg/h and a sulfur removal bed comprising a metal oxide. The reactor is operated at a temperature in the range 280-420° C., preferably 320° C. and a pressure of 10 barg. The sulfur removal bed is operated at a temperature of 160-180° C. The catalyst load was equivalent to a space velocity of 0.8-1.0/h. Average reactor performance at the above conditions was as follows:

| Catalyst Bed Temperature | WHSV | naphtha conversion to liquids | Feed octane | Product Octane increase | Product Sulfur content |
|---|---|---|---|---|---|
| 320° C. | 0.8 | 85% | 58-60 | 22-25 points | 3-5 ppm |

Example 6: 10 Hour Average Catalyst Performance from a Time on Stream of 520-530 Hours The procedure of Example 2 was repeated for the catalyst of Example 1. The reactor was heated to 300° C., and the nitrogen feed was discontinued and 0.4 WHSV of a mixed alkane feed was introduced at a back pressure of 0.34 barg. The reactor was slowly heated to 353° C. The reactor was operated at a temperature in the range 300-350° C. for 520 hours. The reactor temperature was adjusted to 315° C. and the conditions were held constant. The table below is the 10 hour average catalyst performance from a time on stream of 520-530 hours.

Feed composition:
n-hexane: 39% w/w
2-methyl pentane: 24.6% w/w
3-methyl pentane: 14.9% w/w
2,2-dimethyl butane: 2.2% w/w
2,3 dimethyl butane: 3.9% w/w
Methyl-cyclopentane: 9.9% w/w
Cyclohexane: 5.5% w/w

| Catalyst Bed Temperature | WHSV | Conversion to methane/ ethane | Conversion to C$_3$ hydrocarbon | Conversion to C$_4$ hydrocarbon | Conversion to C$_5$+ hydrocarbon |
|---|---|---|---|---|---|
| 325° C. | 0.4 | 0.4% | 7.6% | 6.8% | 85.2% |

The aromatics composition of the liquid (C5+) product on a mass percentage basis is as follows:

| benzene | Toluene | Xylenes | C9 aromatics |
|---|---|---|---|
| 1.6% | 5.7% | 11.9% | 8.3% |

What is claimed is:

1. A process for preparing a composition comprising aliphatic, olefinic, cyclic and/or aromatic hydrocarbons of five or greater carbon atoms per molecule, said process comprising:
   (a) providing a first hydrocarbon mixture comprising isomers of hydrocarbons;
   (b) providing a heterogeneous catalyst, the heterogeneous catalyst comprising:
      (i) pentasil zeolite in a range between about 1% to about 99% by total weight of the heterogeneous catalyst;
      (ii) amorphous silica, amorphous alumina, or a combination thereof, in a range of about 1% to about 99% by total weight of the heterogeneous catalyst;
      (iii) Zn and Cu, independently in a range between about 0.05% to about 3% by total weight of the heterogeneous catalyst; and
      (iv) rhenium in a range of about 0.05% to about 6% by total weight of the heterogeneous catalyst;
   (c) contacting the first hydrocarbon mixture with the heterogeneous catalyst at a temperature increasing from about 300° C. to about 350° C. at rate of about 1° C. per minute; and
   (d) forming a second hydrocarbon mixture comprising molecules having five or more carbon atoms, the second hydrocarbon mixture having a higher octane unit and/or a lower vapor pressure as compared to the first hydrocarbon mixture.

2. The process of claim 1, wherein the second hydrocarbon mixture has a higher octane unit of about 10 to about 25 units.

3. The process of claim 1, further comprising:
stopping forming the second hydrocarbon mixture;
isolating the heterogeneous catalyst; and
regenerating the heterogeneous catalyst to remove carbonaceous deposits.

4. The process of claim 3, wherein the heterogeneous catalyst is at a temperature of about 200° C. to 700° C. during regenerating and the regenerating comprises passing heated wet or dry nitrogen, air or combinations thereof over the heterogeneous catalyst.

5. The process of claim 1, wherein the heterogeneous catalyst is within one or more catalyst beds.

6. The process of claim 5, wherein each bed member comprises one or more first hydrocarbon mixture feed points.

7. The process of claim 6, wherein regenerating the heterogeneous catalyst comprises supplying heated wet or dry nitrogen, air or combinations thereof to each catalyst bed in parallel via the one or more first hydrocarbon mixture feed points.

8. The process of claim 6, wherein contacting the first hydrocarbon mixture with the heterogeneous catalyst further comprises using a temperature control member to control the temperature of the first hydrocarbon mixture, wherein the temperature control member is located on or about the one or more first hydrocarbon mixture feed points.

9. The process of claim 1, further comprising:
heating the first hydrocarbon mixture using one or more cross-exchangers.

10. The process of claim 9, further comprising:
obtaining a liquid, semi-liquid, gaseous or semi-gaseous mixture,
wherein the liquid, semi-liquid, gaseous or semi-gaseous mixture is isolated downstream of the at least one cross-exchanger.

11. The process of claim 1, further comprising:
using a sulfur removal member comprising an adsorbent, wherein the sulfur removal member removes sulfur from the second hydrocarbon mixture; and
operating the sulfur removal member at a temperature capable of sulfur removal.

12. The process of claim 1, further comprising:
obtaining the first hydrocarbon mixture from straight run naphtha derived from a crude oil distillation unit or from a natural gasoline or condensate.

13. The process of claim 1, wherein the pentasil zeolite comprises crystalline aluminosilicate silica/alumina at a mole ratio of between about 15 and about 100.

14. The process of claim 1, further comprising isolating the second hydrocarbon mixture in a drum, absorption tower, or distillation column, or combinations thereof.

15. The process of claim 1, wherein:
contacting the first hydrocarbon mixture with the heterogeneous catalyst in step (c) at a temperature increasing from 300° C. to about 350° is accomplished at a rate of about 1° C. per minute.

16. The process of claim 1, wherein the heterogeneous catalyst is sized to achieve a weight hourly space velocity in the range about 0.01 to about 100.

17. The process of claim 1, further comprising:
providing a dilution stream of liquid petroleum gas (LPG) composition comprising three and/or four carbon atoms per molecule with the first hydrocarbon mixture.

18. The process of claim 1, wherein the heterogeneous catalyst is within at least two catalyst beds.

19. A process for preparing a composition comprising aliphatic, olefinic, cyclic and/or aromatic hydrocarbons of five or greater carbon atoms per molecule, said process comprising:
(a) providing a first hydrocarbon mixture comprising isomers of C5 or C6 hydrocarbons or combinations thereof, and, optionally, a liquid petroleum gas (LPG) composition comprising C3 or C4 hydrocarbons, or combinations thereof;
(b) providing a heterogeneous catalyst, the heterogeneous catalyst comprising:
(i) pentasil zeolite in a range between about 1% to about 99% by total weight of the heterogeneous catalyst;
(ii) amorphous silica, alumina, or a combination thereof in a range of about 1% to about 99% by total weight of the heterogeneous catalyst;
(iii) Zn and Cu, independently in a range between about 0.05% to about 3% by total weight of the heterogeneous catalyst; and
(iv) rhenium in a range of about 0.05% to about 6% by total weight of the heterogeneous catalyst:
(c) contacting the first hydrocarbon mixture with the heterogeneous catalyst at a temperature increasing from about 300° C. to about 350° C. at a rate of about 1° C. per minute; and
(d) forming a second hydrocarbon mixture comprising molecules having five or more carbon atoms, the second hydrocarbon mixture having a higher linear octane number and a lower vapor pressure as compared to the first hydrocarbon mixture.

20. The process of claim 19, wherein the pentasil zeolite comprises crystalline aluminosilicate silica/alumina at a mole ratio of between about 15 and about 100.

21. The process of claim 19, wherein the heterogeneous catalyst is within at least two catalyst beds.

* * * * *